United States Patent [19]

Miller

[11] Patent Number: 5,025,514
[45] Date of Patent: Jun. 25, 1991

[54] PRESSURE MEANS FOR AUTOMATIC HAIR AND SCALP TREATMENT APPARATUS

[75] Inventor: Archie M. Miller, Brentwood, Tenn.

[73] Assignee: IHT, Inc., Nashville, Tenn.

[21] Appl. No.: 504,844

[22] Filed: Apr. 5, 1990

[51] Int. Cl.⁵ ............................................. A45D 19/14
[52] U.S. Cl. .......................................... 4/518; 132/272
[58] Field of Search ................................... 4/515–523; 132/272

[56] References Cited

U.S. PATENT DOCUMENTS 3,416,517 12/1968 Adams et al. ................... 4/516 X
4,834,121 5/1989 Bell ................................. 4/516 X Primary Examiner—Charles E. Phillips
Attorney, Agent, or Firm—Norman L. Wilson, Jr.

[57] ABSTRACT

Automatic hair and scalp treatment machines are known which include a bowl, and a closure therefor, adapted to enclose the head with the face outside the closure. Also included are spray manifolds on an oscillating arcuate header, and driving means imparting partial rotation to the arcuate header. It has been found that dermatoses characterized by the formation of skin cells too rapidly to be eliminated, such as psoriasis, can be treated with this apparatus. Without the machine, removal of the dead cells or plaques is both time consuming and messy. In this treatment it is desirable to begin with low pressure sprays, and increase the pressure to the maximum which the patient can tolerate. One form of apparatus which could be used for this purpose is the machine disclosed in U.S. Pat. No. 4,834,121. In that prior art device the pressure regulator was a conventional regulator ahead of the header. By this invention an adjustable pressure means is provided.

1 Claim, 1 Drawing Sheet

PRESSURE MEANS FOR AUTOMATIC HAIR AND SCALP TREATMENT APPARATUS

BACKGROUND OF THE INVENTION

This invention, in one of its aspects, pertains to apparatus for treating hair and scalp. In another of its aspects the ivention pertains to improvements in the machine characterized in earlier U.S. Pat. No. 4,834,121.

As described in copending application entitled Treatment of Dermatoses it has been foun that dermatoses known as papulosquamous are characterized by the formation of skin cells too rapidly to be eliminated. An example of such diseases is psoriasis. Since the causes and cures of these diseases are not well understood, efforts have been directed to their treatment rather than to their cures. In order to be effective, treatment must first include removal of the scales or plaques. This removal process is both time consuming and messy. The copending application is based upon the discovery that spray can be used to remove the plaques. One form of apparatus which could be used for this purpose is the machine disclosed in U.S. Pat. No. 4,834,121. However that apparatus is a machine operating at a single pressure in the range of 80 psi to 120 psi. As pointed out in that patent the output from a pressure pump flows through a pressure regulator, and at that desired system pressure the fluid flows to spray manifolds. The pressure regulator thus is a conventional regulator which is spring loaded to respond to a pressure drop. Such pressure regulators are responsive to small or sudden changes in incoming fluid pressures, but they operate at a single fixed outlet pressure.

In the treatment of papulosquamous dermatoses it is desirable to begin with low pressure sprays, and increase the pressure to the maximum which the patient can tolerate. Some skin is more sensitive than others. Hence it is preferred to adjust the pressure so that abrading of the plaques can be accomplished without harming bruising or cutting the skin. By this invention such an adjustable pressure means is provided.

SUMMARY OF THE INVENTION

This invention relates to a modification in the hair treating apparatus described in U.S. Pat. No. 4,834,121. That apparatus included a bowl, a closure therefor, adapted to enclose the head with the face outside the closure, and an oscillating arcuate header having nozzles mounted on it to dispense sprays. The arcuate header includes two spray manifolds adapted to oscillate in an arc from a top point opposite the forehead to a bottom point opposite the neck. Means are included, both for imparting partial rotation to the arcuate header to effect such oscillatory movement, and for supplying the treating solutions of the sprays at constant pressure. By this invention pressurized solutions of treating liquids can be supplied to the spray nozzles at pressures which can be increased, to remove scales or plaques, from 80 psi to 120 psi, depending upon the person's toleration pressure. To pump treating solutions to the header under pressure, a closed hydraulic circuit is provided with a pump included in the hydraulic circuit upstream from the header, in the direction of flow. A differential pressure regulator is in the hydraulic circuit down stream from the header, in the direction of flow. The differential pressure regulator opening adjustably restricts flow so that in conjunction with the pump the preselected spray pressure can be attained.

BRIEF DESCRIPTION OF THE DRAWINGS

For a complete understanding of the invention reference to the accompanying drawings.

DETAILED DESCRIPTION OF THE INVENTION

Figure 1:
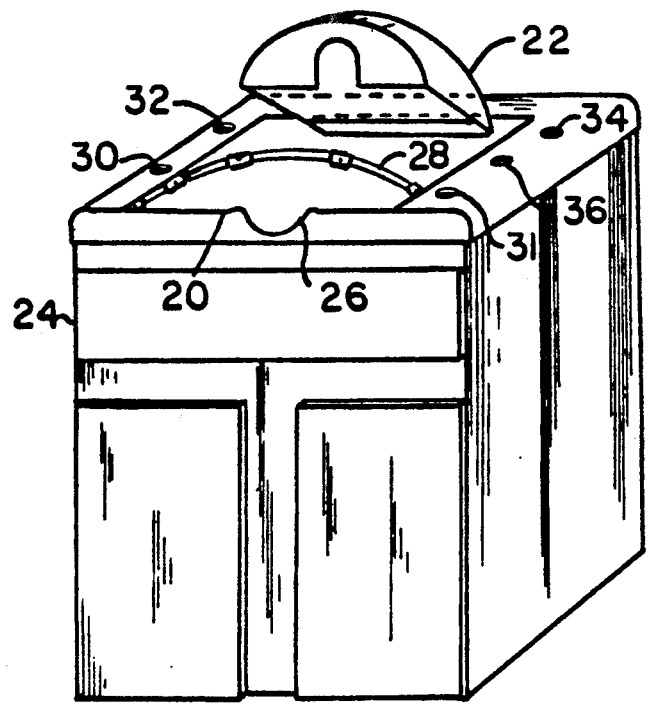
FIG. 1 is a perspective view of the improved machine of this invention.

The general features of the invention are shown in FIG. 1. The automatic hair and scalp treating apparatus includes a shampoo bowl 20 provided with a lid or cover 22, mounted in a cabinet 24. The neck rest is shown at 26. One of the two washing elements or manifolds 28 is visible. The other manifold is disposed at an angle thereto. The manifolds oscillate about an axis or pivot point so that they progress back and forth opposite the head. Control knobs 30, 31, 32, 34 and 36 are also visible in FIG. 1.

Figure 2:
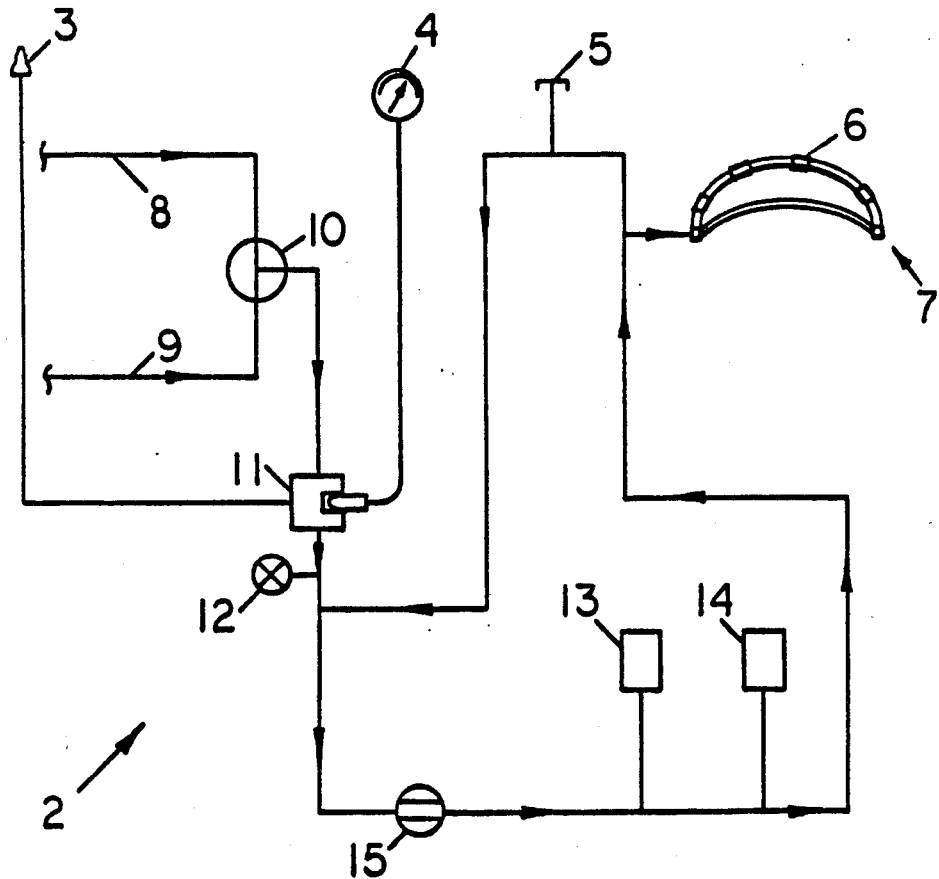
FIG. 2 is a diagrammatic representation of the spray system of the invention incorporated in the apparatus.

Considering now the improved adjustable pressurized hydraulic circuit of this invention, as shown in FIG. 2 hot water and cold water enter the hair and scalp treating machine through lines 8 and 9 respectively. These flow into a, mixing valve 10, and then to a temperature sensing device 11, which maintains an incoming water temperature within two degrees of a set temperature. Normally that temperature is about 109° F., which can be read on temperature gauge 4. The temperature control device 11 can be set to cut off flow if the temperature is outside a preset gauge temperature range. To do so temperature sensor 11 actuates solenoid valve 12. Flow of fluid from the temperature sensing device 11 then continues through pump 15 past cleaning solution additive devices 13 and 14 to header 7 which is positioned in series with pressure regulator 5.

In the treatment of dermatoses, in order better to abrade the scales, it is important to raise the pressure to the maximum which can be tolerated. If subsequent treating compositions will be effective the scales must be removed insofar as is possible to do so. To this end variable spray pressures must be provided. In U.S. Pat. No. 4,834,121 constant pressure sprays were used. The incoming fluids flowing through the temperature sensing device passed through a pressure pump. The output from the this pressure pump then flowed to a pressure regulator. From the pump fluids were passed through a pressure regulator which maintained a fixed pressure within the range set for the action of treating manifolds, for example 80 to 120 psi. From that pressure regulator, the solutions, now at the system pressure, passed to the spray nozzles. In that device the pressure regulator was in balance with the spray, and depended upon nozzle sizes. A single pressure is too abrasive for some patients, and are not sufficienctly abrasive for others.

By the practice of this invention treating solutions do not flow through a constant pressure regulator and then on to the spray nozzles. Rather system pressure is maintained herein by a differential pressure regulator 5 beyond the header 7 in the direction of flow, but in series with the header. It can be seen (FIG. 2) that by adjusting the handwheel of the differential pressure regulator, the spray pressure can be increased to that desired. Differential pressure regular 5 is, in effect, a valve or variable orifice device which can be adjusted to restrict flow of fluid therethrough. Such restriction increases or decreases the pressure of fluid being sprayed through nozzles on spray header 7. If the valve is opened, the pressure of sprays is decreased. The pressure can thus be adjusted from 80 psi with an almost open valve to about 120 psi by almost closing the valve opening. In the case of psoriasis it is desirable to start the treatment at a low pressure, and to increase the pressure to the maximum that the patient can withstand. An advantage of operating the pump, the header, and the differential pressure regulator in series is that the pump is now experiencing the same inlet pressure no matter where the pressure regulator is set, thus prolonging the life of the pump, and of the accompanying pump motor.

Considering now the operation of the apparatus, attention is directed to the four knobs on top of the machine (FIG. 1). The timer switch is set with knob 32, and the lenght of the first cycle (soap or medicine), is set with knob 34. A definite purpose contactor is then energized with start button 30. The fourth knob 36 is a master switch.

With the electric system activated, the hydraulic system is put into operation. Treating solutions will flow through the oscillating manifolds until a timer cam switch closed. This energizes a metering pump for the introduction of soaps or medicines. Additional metering pumps can be brought into operation by other cam switches, and the length of soap or medicine injection is accomplished by a timer 34.

It can be seen that by this invention a machine is provided in which pressurized sprays are reciprocatively impelled against dermatoses plaques. Relative movement between spray and plaques results in a saw-like action which loosens the plaques. By adjusting the pressure of the sprays based on the patient's tolerance, and on the thickness of the plaque layers, the reciprocative spray impingement results in an abrading action removing plaques from the skin much more easily than has been possible heretofore.

In the light of the teachings of this invention variations and modification will occur to those skilled in this field. As indicated, variations are possible in the number and position of manifolds, and in the location and type of nozzle. This is also true of the manifold drive means. Oscillatory movement, whether electrically or hydraulically, can be obtained by a variety of drive mechanisms. Since such ramifications will occur to those working in this field they are deemed to be within the scope of this invention.

What is claimed is:

1. In the apparatus for use in applying hair treating solutions to a person's head, which includes a bowl, a closure therefor adapted to enclose the head with the face outside the closure and the back of the nect on the bowl front, an arcuate header including spray manifolds adapted to oscillate in an arc from a top point opposite the forehead to a bottom point opposite the neck, means imparting partial rotation to the arcuate header to effect said oscillatory movement, a plurality of nozzles disposed on each manifold to dispense adjacent pressurized sprays, and means for supplying treating solutions to the nozzles at constant pressure, the improvement for supplying pressurized solutions of treating liquids to the spray nozzles at pressures which can be adjusted in the range of 80 psi to 120 psi comprising a closed hydraulic circuit including a fluid inlet line, a pump, an adjustable orifice pressure regulator, and a header in series with said pressure regulator, the pump being in the hydraulic circuit upstream from the header, in the direction of flow, to pump fluid to the header under pressure, the adjustable orifice pressure regulator being in the hydraulic circuit downstream from the header, in the direction of flow, the orifice cooperating with the pump to restrict flow thereto, permitting the attainment of a preselected pressure spray at the header by its back pressure.

* * * * *